(12) United States Patent
Fehrenbacher et al.

(10) Patent No.: US 10,251,600 B2
(45) Date of Patent: Apr. 9, 2019

(54) VESSEL DETECTOR AND METHOD OF DETECTION

(71) Applicant: Briteseed LLC, Chicago, IL (US)

(72) Inventors: Paul Fehrenbacher, Chicago, IL (US); Jonathan Gunn, Chicago, IL (US); Hariharan Subramanian, Mundelein, IL (US)

(73) Assignee: Briteseed, LLC, Chicago, IL (US)

( * ) Notice: Subject to any disclaimer, the term of this patent is extended or adjusted under 35 U.S.C. 154(b) by 149 days.

(21) Appl. No.: 15/128,317

(22) PCT Filed: Mar. 24, 2015

(86) PCT No.: PCT/US2015/022244
§ 371 (c)(1),
(2) Date: Sep. 22, 2016

(87) PCT Pub. No.: WO2015/148504
PCT Pub. Date: Oct. 1, 2015

(65) Prior Publication Data
US 2017/0181701 A1    Jun. 29, 2017

Related U.S. Application Data

(60) Provisional application No. 61/970,165, filed on Mar. 25, 2014.

(51) Int. Cl.
*A61B 5/00* (2006.01)
*A61B 17/29* (2006.01)
(Continued)

(52) U.S. Cl.
CPC .......... *A61B 5/4887* (2013.01); *A61B 5/0084* (2013.01); *A61B 5/0086* (2013.01);
(Continued)

(58) Field of Classification Search
CPC ... A61B 17/29; A61B 18/085; A61B 18/1445; A61B 18/1482; A61B 2017/00061;
(Continued)

(56) References Cited

U.S. PATENT DOCUMENTS 5,129,400 A    7/1992  Makino et al.
5,259,761 A    11/1993 Schnettler et al.
(Continued)

FOREIGN PATENT DOCUMENTS

EP    2 353 534    8/2011
GB    1 445 678    8/1976
(Continued)

OTHER PUBLICATIONS

International Search Report and Written Opinion, counterpart PCT application PCT/US2015/022244, 14 pages (dated Sep. 10, 2015).
(Continued)

*Primary Examiner* — George Manuel
(74) *Attorney, Agent, or Firm* — Cook Alex Ltd.

(57) ABSTRACT

A surgical system used to determine if a vessel is within a region proximate to a working end of a surgical instrument includes at least one light emitter disposed at the working end of the surgical instrument, the at least one light emitter adapted to emit light of at least two different wavelengths. The system also includes at least one light sensor disposed at the working end of the surgical instrument opposite the at least one light emitter, the at least one light sensor adapted to detect light at the at least two different wavelengths. The system further includes a controller coupled to the at least one light sensor and adapted to determine a ratio of the light absorbed at the least two different wavelengths, and to indicate if an artifact within a region proximate to the working end of the surgical instrument is a vessel based on the ratio.

20 Claims, 13 Drawing Sheets

(51) Int. Cl.
 *A61B 18/14* (2006.01)
 *A61B 18/08* (2006.01)
 *A61B 17/00* (2006.01)

(52) U.S. Cl.
 CPC ............ *A61B 5/489* (2013.01); *A61B 17/29* (2013.01); *A61B 18/085* (2013.01); *A61B 18/1445* (2013.01); *A61B 18/1482* (2013.01); *A61B 2017/00061* (2013.01); *A61B 2017/2926* (2013.01); *A61B 2505/05* (2013.01)

(58) Field of Classification Search
 CPC ........ A61B 2017/2926; A61B 2505/05; A61B 5/0084; A61B 5/0086; A61B 5/4887; A61B 5/489
 See application file for complete search history.

(56) References Cited

U.S. PATENT DOCUMENTS

| | | |
|---|---|---|
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| 5,987,346 A | 11/1999 | Benaron et al. |
| 6,178,340 B1 | 1/2001 | Svetliza |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,838,210 B2 | 9/2014 | Wood et al. |
| 8,900,219 B2 * | 12/2014 | Sinofsky ............ A61B 5/7264 606/2 |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0111085 A1 | 6/2004 | Singh |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0155194 A1 | 7/2006 | Marcotte et al. |
| 2007/0038118 A1 | 2/2007 | DePue et al. |
| 2009/0018414 A1 | 1/2009 | Toofan |
| 2009/0054908 A1 | 2/2009 | Zand et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0143182 A1 | 6/2012 | Ullrich et al. |
| 2012/0172842 A1 | 7/2012 | Sela et al. |
| 2012/0296205 A1 | 11/2012 | Chernov et al. |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0039309 A1 * | 2/2014 | Harris ............ A61B 5/7282 600/431 |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0236019 A1 | 8/2014 | Rahum |
| 2014/0276088 A1 | 9/2014 | Drucker |
| 2014/0313482 A1 | 10/2014 | Shahidi et al. |
| 2015/0011896 A1 | 1/2015 | Yelin et al. |
| 2015/0051460 A1 | 2/2015 | Saxena et al. |
| 2015/0066000 A1 | 3/2015 | An et al. |
| 2018/0042522 A1 | 2/2018 | Subramanian et al. |
| 2018/0098705 A1 | 4/2018 | Chaturvedi et al. |

FOREIGN PATENT DOCUMENTS

| | | |
|---|---|---|
| JP | H10-005245 | 1/1998 |
| JP | 2003-019116 | 1/2003 |
| JP | 2010-081972 | 4/2010 |
| WO | WO 98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |
| WO | WO2008/082992 | 7/2008 |
| WO | WO 2009/144653 | 12/2009 |
| WO | WO2011/013132 | 2/2011 |
| WO | WO2012/158774 | 11/2012 |
| WO | WO 2013/134411 | 9/2013 |
| WO | WO2014/194317 | 12/2014 |
| WO | WO2016/134327 | 8/2016 |
| WO | WO2016/134330 | 8/2016 |
| WO | WO2017/062720 | 4/2017 |
| WO | WO2017/139624 | 8/2017 |
| WO | WO2017/139642 | 8/2017 |
| WO | WO2018/044722 | 3/2018 |

OTHER PUBLICATIONS

Akl et al., Performance Assessment of an Opto-Fluidic Phantom Mimicking Porcine Liver Parenchyma, J. Bio. Optics, vol. 17(7) 077008-1 to 077008-9 (Jul. 2012).

Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).

Ibey et al., Processing of Pulse Oximeter Signals Using Adaptive Filtering and Autocorrelation to Isolate Perfusion and Oxygenation Components, Proc SPIE, vol. 5702, 54-60 (2005).

(56) References Cited

OTHER PUBLICATIONS

Li et al., Pulsation-Resolved Deep Tissue Dynamics Measured with Diffusing-Wave Spectroscopy, Optics Express, vol. 14, No. 17, 7841-7851 (Aug. 21, 2006).

Mendelson et al., In-vitro Evaluation of a Dual Oxygen Saturation/Hematocrit Intravascular Fiberoptic Catheter, Biomed Instrum. Technol. 24(3):199-206 (May/Jun. 1990).

Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).

Subramanian, Real Time Perfusion and Oxygenation Monitoring in an Implantable Optical Sensor, Thesis Texas A&M Univ. (Dec. 2004).

Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).

Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

\* cited by examiner

VESSEL DETECTOR AND METHOD OF DETECTION

The present application is a U.S. National Stage of PCT International Patent Application No. PCT/US2015/022244, filed on Mar. 24, 2015, which claims priority to Provisional Patent Application No. 61/970,165, filed Mar. 25, 2014, both of which are hereby incorporated herein by reference.

BACKGROUND

This patent is directed to a detector and method for detecting when a vessel is proximate to a surgical instrument or tool, and in particular to a detector and method using the emission and detection of light (such as visible and/or near visible light) for detecting when one of a ureter, a bile duct or a lymphatic vessel is proximate to a surgical instrument or tool.

The identification of artifacts, and in particular vessels, during surgical procedures can provide valuable information for the surgeon or surgical team. For instance, identification of a blood vessel from a vessel that carries a fluid other than blood may permit the non-blood carrying vessel to be avoided, minimizing the chances of injury to the non-blood carrying vessel. Alternatively, identification of the blood vessels and the non-blood carrying vessels may permit the non-blood carrying vessel to be isolated, instead of avoided.

In regard to identification of the vessel to avoid injury, consider the opportunity for iatrogenic ureteral injury during gynecological, urological and other pelvic region surgeries. Such an injury may occur as a consequence of the surgical procedure. Additionally, because the ureters course close to major blood vessels, such as the uterine arteries, ureteral injury can occur as a consequence of attempts to control bleeding. In particular, when inadvertent intraoperative bleeding obstructs the surgeon's field of view, the surgeon's attempts to control the bleeding by cauterizing, clamping or suturing the blood vessels can lead instead to ureteral injury.

Given the proximity of major blood vessels to the ureters and the obstruction of the surgeon's field of view should bleeding occur, injuries can occur even when the surgeon has a sound understanding of normal anatomy. Aberrant ureteral anatomy occurs in up to 8% of the population, however. When combined with the other factors, the surgeon faces a considerable challenge.

A systematic review of gynecological procedures has determined that ureteral injury occurs in 0.03% to 2.0% of abdominal hysterectomies, 0.02% to 0.5% of vaginal hysterectomies and 0.2% to 6.0% of laparoscopic-assisted vaginal hysterectomies. Considering the factors addressed above, perhaps these figures are not surprising. Because of the physiological importance of the renal system and the significant negative consequences of injury to the same, these rates are particularly sobering.

Ureteral injury can lead to ureteral obstruction (for example, if the ureter is ligated) or discontinuity (if the ureter is resected). If an injury to the ureter has occurred and is unrecognized (for example, if the ureter is crushed), it may lead to the formation of fistulas in addition to obstruction. Certainly, ureteral injury can lead to significant patient morbidity and mortality. In any event, ureter injury will increase the likelihood of hospitalization (if the procedure is performed on an outpatient basis), as well as the duration of the hospital stay.

Also in regard to identification of a vessel to avoid its injury, consider the treatment of gallstone development through surgical intervention, which is quite common in the United States with approximately 400,000 cholecystectomies performed annually. One important complication of these procedures is bile duct injury. The bile duct, which carries bile from the liver to the intestines, is disposed in close proximity to the gallbladder. Furthermore, the bile duct is buried under fatty tissue that may prevent the surgeon from directly visualizing the duct.

The estimated incidence of bile duct injury in laparoscopic cholecystectomies (which account for nearly 90% of all cholecystectomies performed in the United States) is between 0.3 to 2.7%. Again, because of the importance of the bile system and the significant negative consequences of injury, this rate is significant.

Mild injuries to the bile duct may include cystic duct leakage and bile duct strictures. Major injuries include more significant amounts of leakage and even complete transection of the common bile duct itself. Leakage of bile into the peritoneum can lead to a painful and potentially dangerous infection. While mild injuries may be treated endoscopically and/or interventionally, major injuries often require open surgery, such as hepaticojejunostomy. Thus, injuries to the bile duct (especially major injuries that may require open surgery) may increase the duration of the hospital stay and the length of the time for the patient to return to full activity after the procedure.

In regard to identification of the vessel to facilitate its isolation, sentinel lymph biopsy (SLNB) has been increasingly used while staging lymph node metastasis. Breast cancer, melanoma and gastrointestinal cancer malignancies have all been successfully staged using SLNB. SLNB provides accurate staging information with less morbidity than the previous widely-accepted technique of formal surgical dissection of the draining lymph node basin. However, SNLB requires proper identification of the sentinel lymph node.

As set forth in more detail below, the present disclosure describes a surgical system including a vessel detector and method of detecting a vessel embodying advantageous alternatives to the existing methods, which may provide for improved identification for avoidance or isolation of the vessel.

SUMMARY

According to one aspect of the present disclosure, a surgical system used to determine if a vessel is within a region proximate to a working end of a surgical instrument, includes at least one light emitter disposed at the working end of the surgical instrument, the at least one light emitter adapted to emit light of at least two different wavelengths. The system also includes at least one light sensor disposed at the working end of the surgical instrument opposite the at least one light emitter, the at least one light sensor adapted to detect light at the at least two different wavelengths. The system further includes a controller coupled to the at least one light sensor and adapted to determine a ratio of the light absorbed at the least two different wavelengths, and to indicate if an artifact within a region proximate to the working end of the surgical instrument is a vessel based on the ratio.

According to another aspect of the present disclosure, a method of determining if a vessel is within a region proximate to a working end of a surgical instrument includes emitting light of at least two different wavelengths at the working end of the surgical instrument, and sensing light of at least two different wavelengths at the working end of the surgical instrument. The method further includes determining a ratio of the light absorbed at the least two different wavelengths; and indicating if an artifact within a region proximate to the working end of the surgical instrument is a vessel based on the ratio.

According to a further aspect of the present disclosure, a surgical system used to determine if one of a ureter, a bile duct or a lymphatic vessel is within a region proximate to a working end of a surgical instrument includes at least one light emitter disposed at the working end of the surgical instrument, the at least one light emitter adapted to emit light of at least two different wavelengths. The system also includes at least one light sensor disposed at the working end of the surgical instrument opposite the at least one light emitter, the at least one light sensor adapted to detect light at the at least two different wavelengths. The system further includes a controller coupled to the at least one light sensor and adapted to determine a ratio of the light absorbed at the least two different wavelengths, and to indicate if an artifact within a region proximate to the working end of the surgical instrument is one of a ureter, a bile duct or a lymphatic vessel based on the ratio.

According to still another aspect of the present disclosure, a method of determining if one of a ureter, a bile duct or a lymphatic vessel is within a region proximate to a working end of a surgical instrument includes emitting light of at least two different wavelengths at the working end of the surgical instrument, and sensing light of at least two different wavelengths at the working end of the surgical instrument. The method further includes determining a ratio of the light absorbed at the least two different wavelengths; and indicating if an artifact within a region proximate to the working end of the surgical instrument is one of a ureter, a bile duct or a lymphatic vessel based on the ratio.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Figure 1:
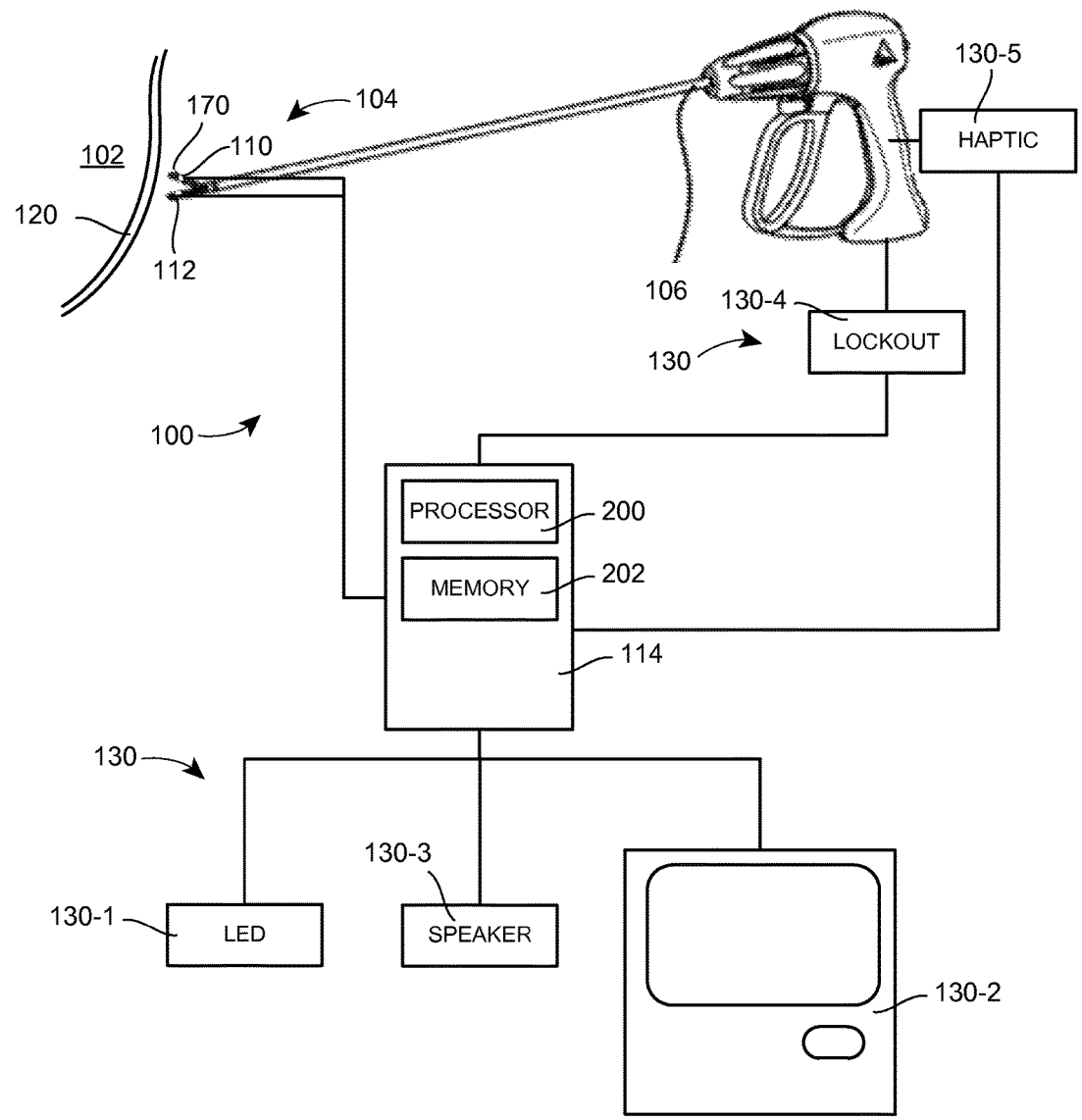
FIG. 1 is a schematic of a surgical system according to an embodiment of the present disclosure.

FIG. 1 illustrates a surgical system 100 used to determine if a ureter is within a region 102 proximate to a working end 104 of a surgical instrument 106. The surgical system 100 includes at least one light emitter 110 (or simply the light emitter 110), at least one light sensor 112 (or simply the light sensor 112), and a controller 114 coupled to the light emitter 110 and the light sensor 112. The light emitter 110, light sensor 112 and the controller 114 may be referred to as a ureter detector.

The light emitter 110 is disposed at the working end 104 of the surgical instrument 106 as noted above. The light emitter 110 is adapted to emit light of at least two different wavelengths. This may be achieved through the use of a single element, or a plurality of elements (which elements may be arranged or configured into an array, for example). In a similar fashion, the light sensor 112 is disposed at the working end 104 of the surgical instrument 106 opposite the at least one light emitter 110. The light sensor 112 is adapted to detect light at the at least two different wavelengths. This may also be achieved through the use of a single element, or a plurality of elements (which elements may be arranged or configured into an array, for example).

The controller 114 is adapted to determine a ratio of the light absorbed at the least two different wavelengths, and to indicate if an artifact 120 within a region 102 proximate to the working end 104 of the surgical instrument 106 is a ureter based on the ratio. Instead of being a ureter, the artifact (or structural artifact) may be a blood vessel or a tissue. To signal or indicate that the artifact 120 within the region 102 is a ureter, the controller 114 may be coupled to an output device or indicator 130, which may provide a visible, audible, tactile or other signal to the user of the instrument 106.

Figure 2:
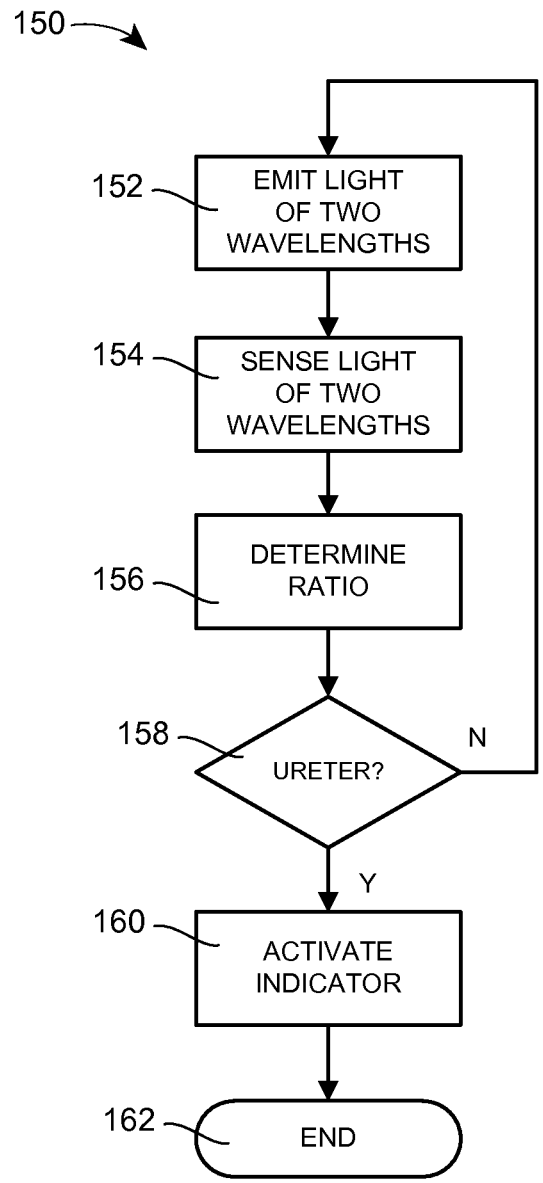
FIG. 2 is a flow chart of a method of detecting a ureter according to an embodiment of the present disclosure, which method may be carried out using the system of FIG. 1.
Figure 3:
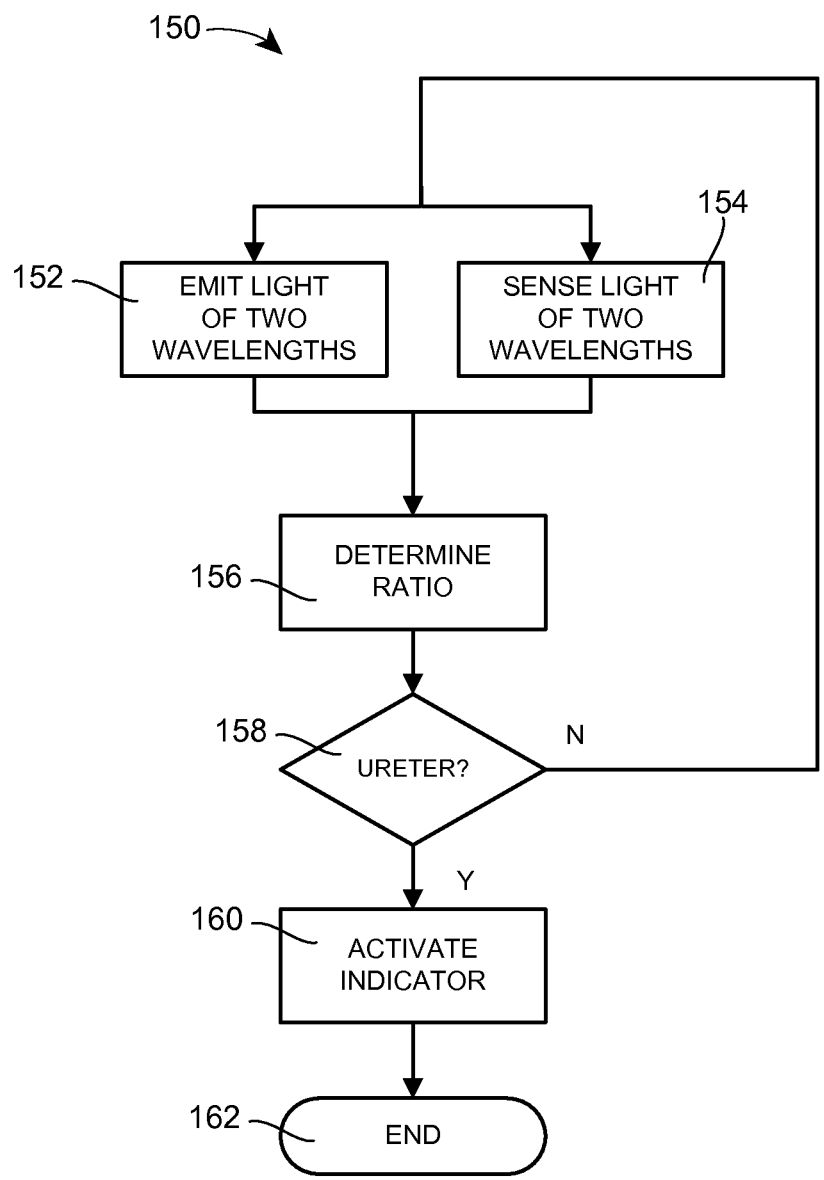
FIG. 3 is a flow chart of another method of detecting a ureter according to an embodiment of the present disclosure, which method may be carried out using the system of FIG. 1.

As reflected in the flowcharts of FIGS. 2 and 3, a method 150 of determining if a ureter is within a region 102 proximate to a working end 104 of a surgical instrument 106 is illustrated, and may be carried out using the surgical system 100 described in regard to FIG. 1. The method 150 begins at block 152, wherein light of at least two different wavelengths is emitted at the working end 104 of the surgical instrument 106, for example using the light emitter 110. The method 150 continues and/or also begins at block 154, wherein light of at least two different wavelengths is sensed at the working end 104 of the surgical instrument 106, for example using the light sensor 112. That is, the light may be emitted and detected successively using electronic multiplexing (see FIG. 2) or simultaneously via use of optical filters (see FIG. 3). The method 150 further includes determining a ratio of the light absorbed at the at least two different wavelengths at block 156, determining if an artifact is a ureter at block 158 based on the ratio, and indicating if an artifact 120 within a region 102 proximate to the working end 104 of the surgical instrument 106 is a ureter based on the ratio at block 160, which actions may be performed by the controller 114 and the indicator 130.

If it is determined at block 158 that the artifact is not a ureter, the method 150 may return to block 152, to repeat the actions of blocks 152-158, as illustrated in either of the flowcharts of FIGS. 2 and 3. Furthermore, if the artifact is a ureter and the indicator is activated at block 160, the method 150 may end at a block 162, as is also illustrated. For example, according to an embodiment of the method 150 where the indicator is a lockout device which disables the medical instrument 106, the method 150 may end at block 162 once the lockout device has been activated.

Alternatively, the method 150 may return to block 152 once the indicator has been activated at block 160. See, e.g., FIG. 4. For example, according to an embodiment wherein the indicator is a speaker that generates an audible alarm, the method 150 may activate the indicator/speaker at block 160 for a period of time (e.g., 1-2 seconds), then repeat the actions of blocks 152-158 and activate the indicator at block 160 again if the determination is made at block 158 that the ureter is in the region 102. If the blocks 152-158 are repeated and the ureter is not in the region 102, then the method 150 would not proceed to the block 160 and the indicator would not be re-activated according to such an embodiment. While this alternative embodiment has been illustrated with blocks 152, 154 arranged as in FIG. 2, the alternative embodiment could be similarly used with blocks 152, 154 arranged as in FIG. 3.

Figure 5:
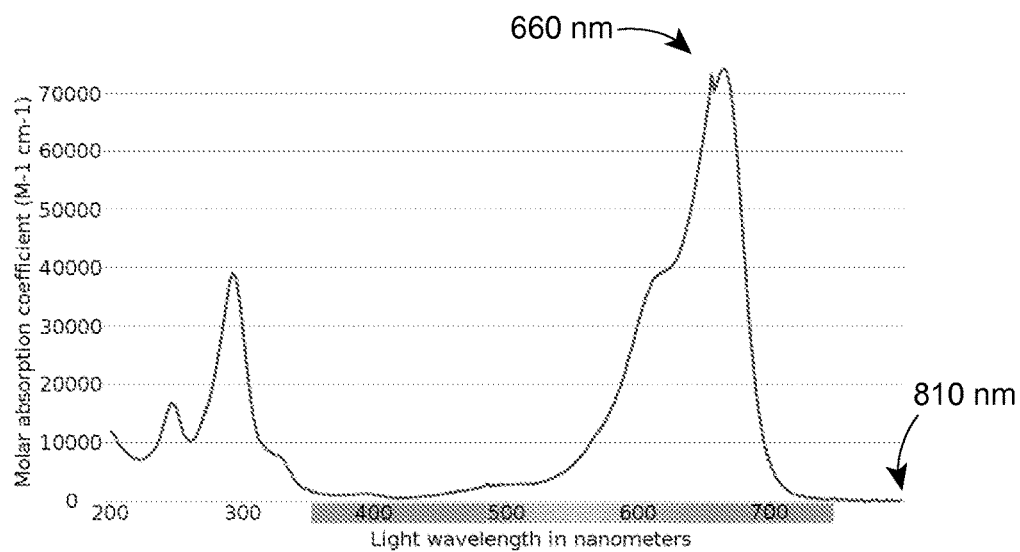
FIG. 5 is a chart illustrating the light absorption spectrum of methylene blue.
Figure 6:
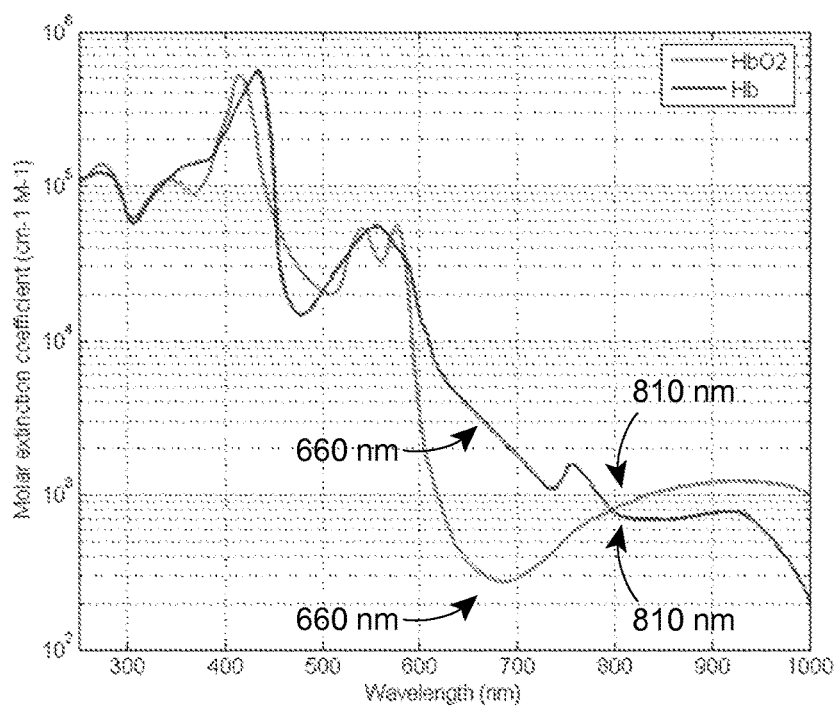
FIG. 6 is a chart illustrating the light absorption spectrum of blood.

The embodiments of the present disclosure according to FIGS. 1-4 may be discussed in general terms as follows. Light of different wavelengths is absorbed by blood (within blood vessels or potentially bleeding from the blood vessels into the surgeon's field of view), static tissue (e.g., fat, connective tissue, etc.) or the ureter to different extents. By selecting a pair of wavelengths where the absorption of light is similar for blood but significantly different for fluid in the ureter (e.g., a dye or urea), the system 100 and method 150 may differentiate between blood or a blood vessel and a ureter. For example, if a contrast agent such as methylene blue is administered to the patient (which collects quickly in the ureter), the ratio of light absorbed at wavelengths of 660 nm and 810 nm will be large for the ureter (e.g., greater than 10) and small for blood or a blood vessel (e.g., potentially less than 1). Compare FIGS. 5 and 6. As a consequence, a relatively robust differentiation may be made between an artifact 120 in the form of a ureter and blood in the surgeon's field of view.

Having thus described the surgical system 100 (with ureter detector), the method 150 of detection of a ureter (which may be carried out using the surgical system 100) and the principles of the system 100 and the method 150 in general terms, further details of the system 100 and its operation are provided.

Initially, while the emitter 110 and the sensor 112 are described as disposed at the working end 104 of the surgical instrument 106, it will be recognized that all of the components that define the emitter 110 and the sensor 112 need not be disposed at the working end of the instrument 106. That is, the emitter 110 may comprise a light emitting diode, and that component may be disposed at the working end 104. Alternatively, the emitter 110 may include a length of optical fiber and a light source, the source disposed remotely from the working end 104 and the fiber having a first end optically coupled to the source and a second end disposed at the working end 104 facing the sensor 112. According to the present disclosure, such an emitter 110 would still be described as disposed at the working end 104 because the light is emitted from the ureter detector into the tissue at the working end 104 of the instrument 106. A similar arrangement may be described for the sensor 112 wherein an optical fiber has a first end disposed facing the emitter 110 (or perhaps more particularly, an end of the optical fiber that in part defines the emitter 110) and a second end optically coupled to other components that collectively define the sensor 112.

As also mentioned above, the light emitter 110 and light sensor 112 are positioned opposite each other. This does not require the emitter 110 and the sensor 112 to be directly facing each other, although this is preferred. According to certain embodiments, the emitter 110 and sensor 112 may be formed integrally (i.e., as one piece) with the jaws 170 of a surgical instrument 106. See FIGS. 1, 7 and 8. In this manner, light emitted by the emitter 110 between the jaws 170 and through the tissue of interest may be captured by the light sensor 112.

As to those embodiments wherein the light emitter 110 is in the form of one or more light emitting diodes, for example, disposed at the working end 104 of the instrument 106, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 112 may also include one or more elements. According to an embodiment schematically illustrated in FIGS. 7 and 8, the light sensor 112 may include a first light sensor 112-1 and a second light sensor 112-2. The first light sensor 112-1 may be adapted to detect light in the visible range, and a second light sensor 112-2 may be adapted to detect light in the near-infrared range. For example, the first light sensor 112-1 may be adapted to detect light at 600 nm or 660 nm, and the second light sensor 112-2 may be adapted to detect light at 810 nm. Such an embodiment may be used where a dye has been used. For example, indigo carmine has a characteristic light absorption at 600 nm, while methylene blue has a characteristic light absorption at 660 nm (see FIG. 5). These dyes have the benefit that they are typically used for the visual identification of ureter and bladder leakage during surgery, and thus do not represent an additional burden in terms of additional procedural steps or expense.

Figure 4:
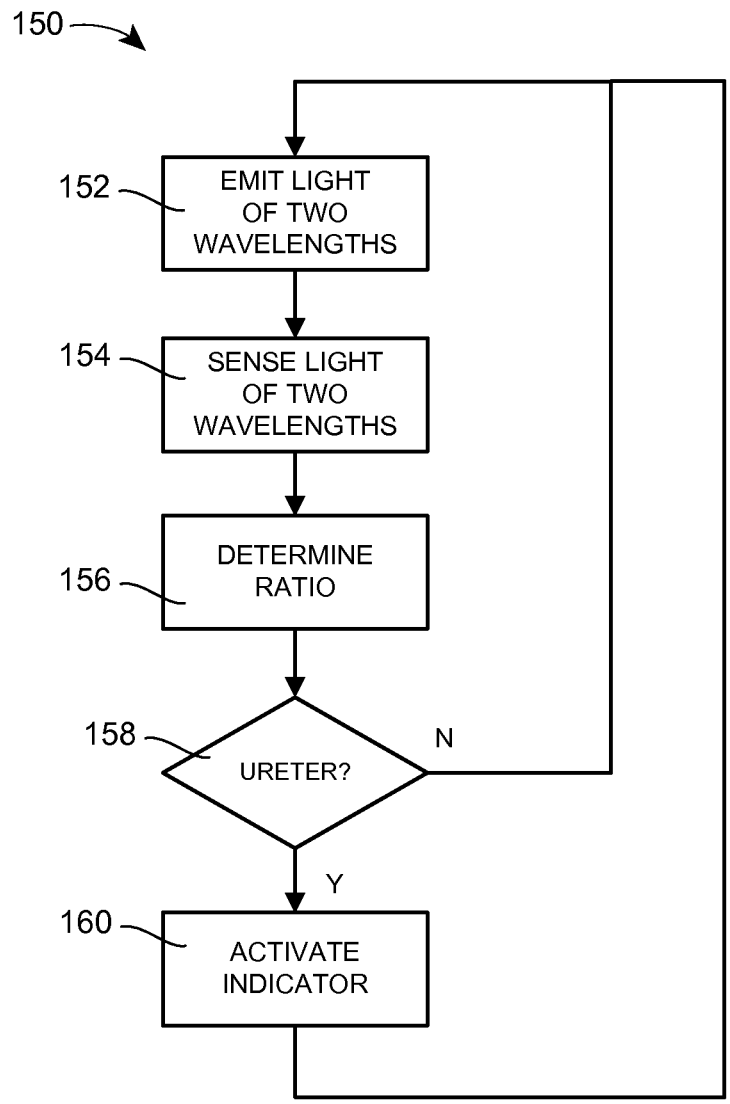
FIG. 4 is a flow chart of a further method of detecting a ureter according to an embodiment of the present disclosure, which method may be carried out using the system of FIG. 1.
Figure 9:
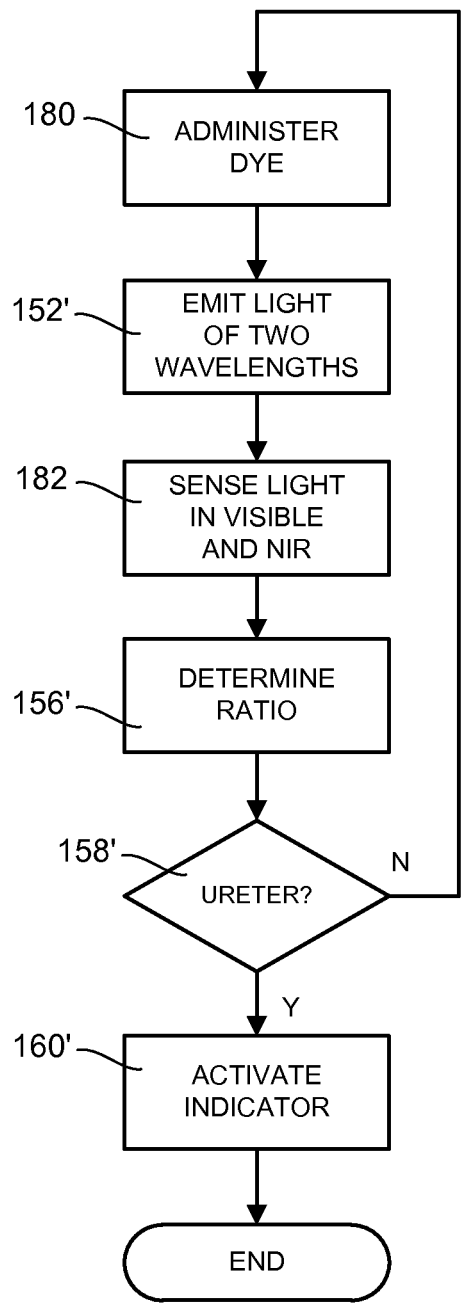
FIG. 9 is a flow chart of an alternative method of detecting a ureter according to an embodiment of the present disclosure, which method may be carried out using the system of FIG. 1.

In regard to such an embodiment, the method of FIGS. 2-4 may further include administering a dye (block 180), and the sensing of the light of at least two different wavelengths (at block 154) comprises sensing light at a first wavelength in the visible range and at a second wavelength in the near-infrared range (block 182). See FIG. 9, wherein the steps in common with the method 150 are indicated using common reference numerals further marked with a prime. The agents mentioned above, indigo carmine and methylene blue, may be injected into the blood stream, and then quickly accumulate in the kidneys, where the agents and/or their derivatives are excreted by the renal system in urine through the ureters, bladder and urethra (in this regard, it will be recognized that certain agents may be metabolized in the body; for example, methylene blue is excreted as leukomethylene blue by the kidneys). On the other hand, if the dye is administered continuously intravenously throughout a surgery, the ureter may be identified throughout the surgery, and not simply within a particular time window after a bolus injection has been administered, which is an advantage particular to this system 100 and method.

It also will be noted that the surgical system 100 according such an embodiment provides the advantage of permitting differentiation between not only blood in blood vessels, but blood in the surgical field. As mentioned above, there is often a loss of direct visualization of the ureters because of blood obstructing the surgeon's field of view. In this case, the use of the ratio(s), between light in the visible spectrum and light in the infrared or near-infrared spectrum, in combination with the high absorptivity of infrared light by urea or near-infrared light by dyes (such as methylene blue) permits a robust differentiation to be made between the ureter and the stagnant blood in the surgeon's field of view. Consequently, it is believed that stagnant blood will not represent a significant obstacle for the surgeon using the system 100 and method 150 according to the present disclosure.

It is further noted that though dye may be used, if the dye becomes present in the surgical field in the form of stagnant blood for example, it is believed that the surgical instrument according to the above embodiments may still differentiate the dye present in the blood from the dye in the ureter. First, the concentration of dye in the blood vessel, and thus in the stagnant blood, is more dilute than that found in the kidneys and resultantly in the ureters. As a consequence, any variance in the light measured and the resultant signal passed to the controller may be filtered as noise. Second, dyes such as methylene blue have a modified absorption profile at different levels of acidity or basicity, which levels are normally expressed in terms of pH. For example, blood has a pH of approximately 7.3 (relatively neutral), while urine has a pH of 4.6 (acidic). This permits the wavelengths to be used in determining the ratio to be selected in such a manner as to increase the likelihood that a determination that an artifact is a ureter is an accurate determination even if there is dye present in blood as well.

Figure 7:
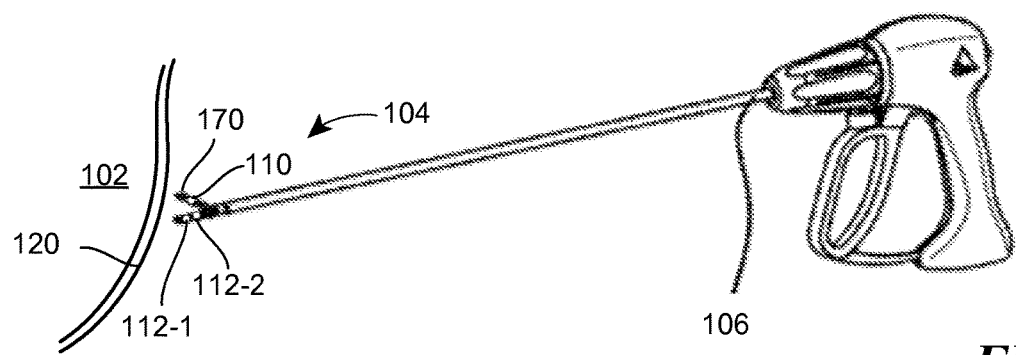
FIG. 7 is a schematic of a surgical instrument with light emitter and light sensors according to an embodiment of the present disclosure.
Figure 8:
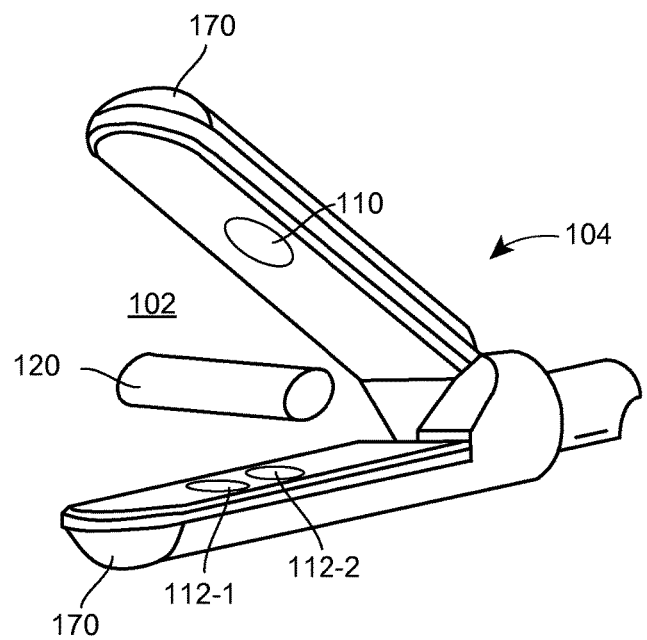
FIG. 8 is an enlarged, fragmentary view of the surgical instrument with light emitter and light sensors according to FIG. 7 with a section of an artifact illustrated as disposed between the light emitter and light sensors.
Figure 10:
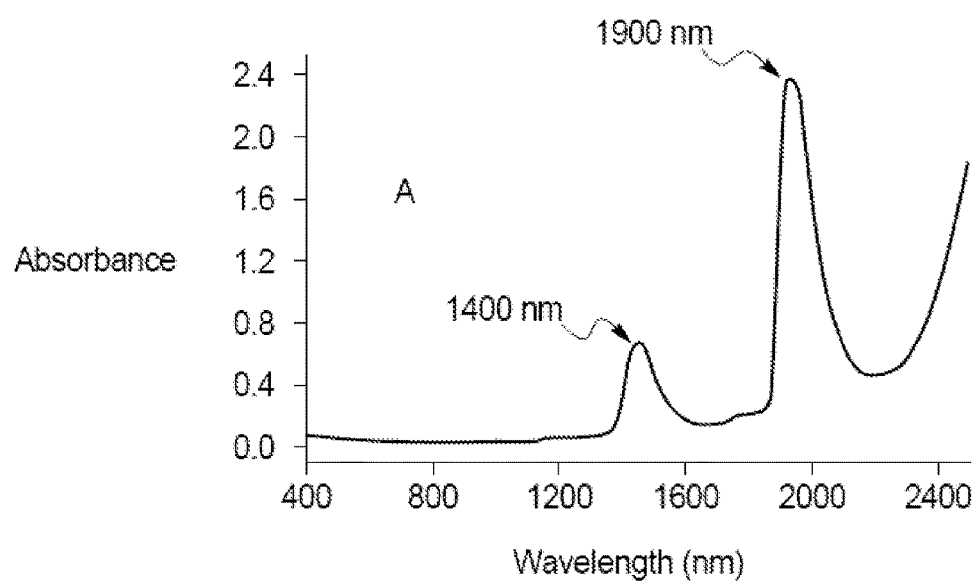
FIG. 10 is a chart illustrating the light absorption spectrum of urea.

According to another embodiment such as may be schematically illustrated in FIGS. 7 and 8, the light sensor 112 includes a first light sensor 112-1 adapted to detect light in the visible range, and a second light sensor 112-2 adapted to detect light in the infrared range above the near-infrared range. For example, the second light sensor is adapted to detect light between 1400 nm and 1900 nm. Such an embodiment may be used where no dye has been used, and the system and method are instead being used to detect the presence of urea in the artifact of interest, urea having a characteristic light absorption at 1400 nm and 1900 nm. See FIG. 10. Such a system would advantageously provide a robust differentiation between the ureter and stagnant blood, while avoiding the necessity of addressing dye in blood within the blood vessel or in blood that is obscuring the surgeon's field of view.

In either event, the surgical system 100 described herein does not require the need for costly fluorescent imaging agents or equipment designed to detect such agents. Instead, the system 100 may be used without dyes, or may be used in conjunction with absorptive dyes which would already be used in the surgery even if the dye was not also being used to detect the presence of the ureter proximate to the surgical instrument.

According to a still further embodiment, the controller 114 may be adapted to utilize other characteristics in the determination as to whether the artifact 120 is a ureter. For example, the controller 114 may be adapted to determine a characteristic pulsation of an artifact 120 within a region 102 proximate to the working end 104 of the surgical instrument 106 based on the light detected by the at least one light sensor 112, and to indicate if the artifact 120 is a ureter based on the ratio and the characteristic pulsation. The difference in the pulsation of the artifact 120 may be combined with the light absorption information to determine if the artifact 120 is a ureter (or, for example, a blood vessel).

For example, a blood vessel may be described as having a characteristic pulsation of approximately 60 pulses (or beats) per minute. While this may vary with the patient's age and condition, the range of pulsation is typically between 60 and 100 pulses (or beats) per minute. On the other hand, a ureter has a characteristic pulsation (i.e., normal peristalsis) of between 1 and 8 pulses per minute. If a dye, for example, is circulating through the ureter, the light sensor 112 will produce a signal (that is passed to the controller 114) with a particular AC waveform that corresponds to the movement of the dye through the artifact 120. Given the relatively disparate ranges between the characteristic pulsations for a blood vessel and a ureter, a robust determination may be made as to the determination whether an artifact 120 may be classified as a ureter.

In fact, the surgical system 100 additionally may include a sensor or sensors that can be coupled to and used by the controller 114 to determine a heart rate reading, or that may provide (via other circuitry or controllers/processors) a heart rate reading to the controller 114. For example, the system 100 may include an electrocardiography (EKG) device, or a pulse oximeter that is disposed on the patient's finger or ear. The controller 114 may receive a heart rate waveform from the EKG device or the pulse oximeter (via other circuitry or controllers/processors) or may use information from the EKG device or the pulse oximeter to generate a heart rate waveform that can be compared against the AC waveform mentioned above to determine if the characteristic pulsation is associated with a blood vessel or a ureter. Alternatively, the controller 114 may receive a frequency associated with the heart rate from the sensor or sensors (via the optional circuitry or controllers/processors), and use this frequency to determine if the characteristic pulsation is associated with a blood vessel or a ureter. This may provide additional accuracy in the comparison, as well as for those patients that may suffer from an irregular heartbeat.

Figure 11:
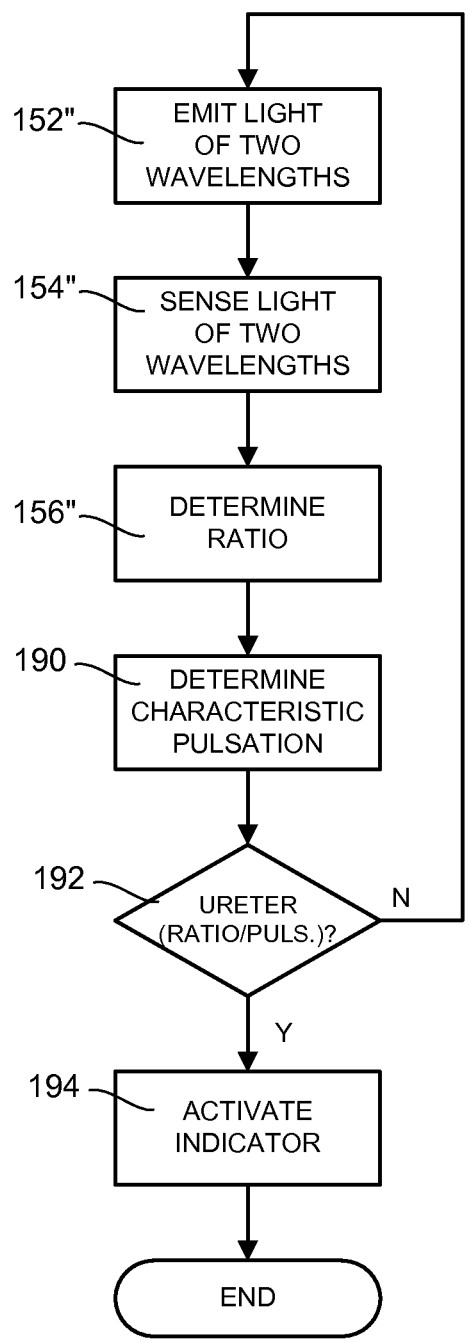
FIG. 11 is a flow chart of a further alternative method of detecting a ureter according to an embodiment of the present disclosure, which method may be carried out using the system of FIG. 1.

This configuration of the controller 114 may also be phrased in terms of a method of detection as illustrated in FIG. 11, similar to the method illustrated in FIGS. 2-4 wherein common elements are numbered similarly except for a double prime. While the method is described relative to the embodiment of the method 150 illustrated in FIG. 2, it will be recognized that it could also be described relative to the embodiments in FIGS. 3 and 4 as well. Thus, the method of FIG. 11 includes a block 190 wherein a characteristic pulsation of an artifact 120 within a region 102 proximate to the working end 104 of the surgical instrument 106 is determined based on the light detected by the light sensor 112. The method also includes a block 192 wherein a determination is made whether the artifact 120 is a ureter based on the ratio and the characteristic pulsation, and a block 194 wherein an indication is made if the artifact 120 is a ureter.

It will also be recognized that the characteristic pulsation may be used separate and apart from the ratio to determine if an artifact is a ureter. For example, the characteristic pulsation may be combined with the relative location of the system 100 and the working tip 104 of the surgical instrument 106 to determine if an artifact 120 is a ureter. If the system 100 is being used in close proximity to the kidneys, for example, the characteristic pulsation may be used alone to determine the presence of a ureter.

According to the foregoing embodiments, the controller 114 may include a processor 200 and memory 202, and the processor 200 may be programmed to determine a ratio of the light absorbed at the least two different wavelengths, and to indicate if an artifact within a region proximate to the working end of the surgical instrument is a ureter based on the ratio. In a similar fashion, the processor 200 may be programmed to determine a characteristic pulsation of an artifact 120 within a region 102 proximate to the working end 104 of the surgical instrument 106 based on the light detected by the light sensor 112, and to indicate if the artifact 120 is a ureter based on the ratio and the characteristic pulsation. Alternatively, the controller 114 may include circuits or circuitry that is adapted to carry out such actions.

As for the indicator 130 used in conjunction with controller 114, a variety of output devices may be used. For example, a light emitting diode 130-1 may be attached to or incorporated into the associated surgical instrument 106, and may even be disposed at the working end 104 of the instrument 106. Alternatively, an alert may be displayed on a video monitor 130-2 being used for the surgery, or may cause an image on the monitor to change color or to flash, change size or otherwise change appearance. The indicator 130 may also be in the form of or include a speaker 130-3 that provides an auditory alarm. The indicator 130 also may be in the form of or may incorporate a safety lockout 130-4 associated with the surgical instrument 106 that interrupts use of the instrument 106. For example, the lockout could prevent ligation or cauterization where the surgical instrument 106 is a thermal ligature device. As a still further example, the indicator 130 also may be in the form of a haptic feedback system, such as a vibrator 130-5, which may be attached to or formed integral with a handle or handpiece of the surgical instrument 106 to provide a tactile indication or alarm. Various combinations of these particular forms of the indicator 130 may also be used.

It should be clear that the surgical system 100 may also include the surgical instrument 106 with the working end 104, to which the light emitter 110 and light sensor 112 are attached (in the alternative, removably or permanently/ irreversibly). The light emitter 110 and the light sensor may instead be formed integrally (i.e., as one piece) with the surgical instrument 106. It is further possible that the light emitter and light sensor be attached to a separate instrument or tool that is used in conjunction with the surgical tool 106. As noted above, the surgical instrument 106 may be a thermal ligature device.

In the alternative to the foregoing, the system 100 may be used to determine if a ureter is within a region 102 proximate to a working end 104 of a surgical instrument 106 using a single wavelength. According to such an embodiment, the light emitter 110 is adapted to emit light of a single wavelength or channel (e.g., 660 nm or 1400 nm). In a similar fashion, the light sensor 112 disposed at the working end 104 of the surgical instrument 106 opposite the light emitter 110 is adapted to detect light at the single wavelength.

Because only a single wavelength is used, the system 100 would not determine if an artifact 120 is or is not a ureter based on a ratio of light of different wavelengths received at the light sensor 112. Instead, the controller 114 may determine if the light at the light sensor 112 exceeds a threshold determined in advance (i.e., a predefined threshold). Because of the high absorption of light by urea at wavelengths between 1000 nm to 1400 nm and by methylene blue at approximately 660 nm relative to blood, if the light sensed exceeds a particular threshold at either of these wavelengths or wavelength ranges, then an artifact 120 in the region 102 is most likely a ureter. Such a threshold may be determined experimentally, for example by conducting a series of in vivo tests with the system 100.

In a single wavelength system such as the system 100, knowledge of the brightness of the illuminating light is necessary to calculate the absolute absorbance of the tissue. Consequently, the input (or illuminated) light should be kept constant. If the light illumination cannot be kept constant, the light illumination should be calibrated using a predefined algorithm. The predefined algorithm is used to correlate the voltage of the light source with its light output so that the illuminating light brightness may be known. In a multiple wavelength system such as the system 100, light brightness is eliminated as a factor as a consequence of the ratio used.

Figure 12:
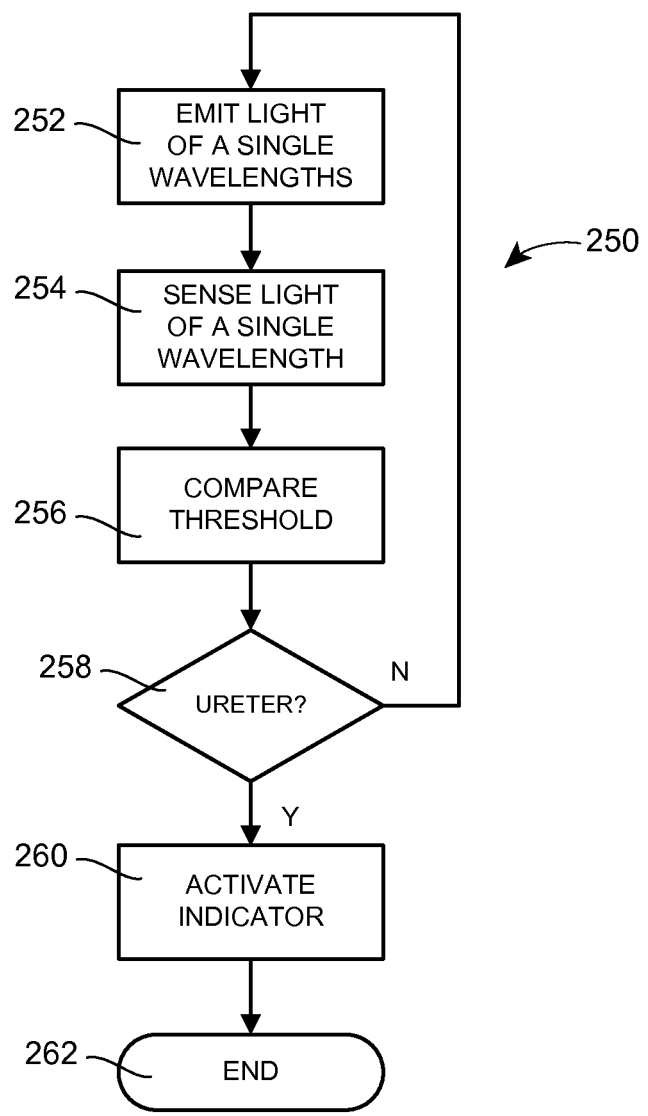
FIG. 12 is a flow chart of a still further alternative method of detecting a ureter according to an embodiment of the present disclosure, which method may be carried out using the system of FIG. 1.

According to a method 250 illustrated in FIG. 12, the method begins at block 252 with the emission of light at a single wavelength by the light emitter 110, and the detection of the light by the light sensor 112 at block 254. As illustrated in FIGS. 2 and 3, the actions of blocks 252, 254 may occur sequentially or concurrently. At block 256, the light at the light sensor 112 is compared with a threshold at block 256, and a determination is made at block 258 if an artifact 120 is a ureter. If the determination is made at block 258 that the artifact 120 is a ureter, the indicator 130 is activated at block 260, and the method 250 may end at block 262. Alternatively, the method 260 may return to block 252, similar to the embodiment of method 150 illustrated in FIG. 4. The method 250 may also return to block 252 if it is determined at block 258 that the artifact 120 is not a ureter.

As a further alternative, it will be recognized that while the system 100 described herein has been used for detecting a ureter (i.e., for determining if an artifact 120 in a region 102 proximate to a working end 104 of the surgical instrument 106 is a ureter), the system 100 may be used to detect other tissues as well, through the use of a ratio of absorption and/or characteristic pulsations. For example, the system 100 may be used for detecting a bile duct or a lymphatic vessel. The methods described above may be used as well, as is particularly described below by way of example and not by way of limitation.

Such a system may still include at least one light emitter disposed at the working end of the surgical instrument, the at least one light emitter adapted to emit light of at least two different wavelengths, and at least one light sensor disposed at the working end of the surgical instrument opposite the at least one light emitter, the at least one light sensor adapted to detect light at the at least two different wavelengths. The system would include, however, a controller coupled to the at least one light sensor and adapted to determine a ratio of the light absorbed at the least two different wavelengths, and to indicate if an artifact within a region proximate to the working end of the surgical instrument is a particular type of tissue based on the ratio. Alternatively, the controller may additionally determine a characteristic pulsation of the artifact based on the light detected by the one light sensor, and indicate if the artifact is a ureter based on the ratio and the characteristic pulsation. The first and second wavelengths used according to such a system would be tailored to the particular tissue in the same regard that the particular wavelengths mentioned above were selected for use with dyes or urea present in the artifact of interest, the ureter.

For example, in regard to bile duct identification, indocyanine green (ICG) fluorophore (e.g., indocyanine green/ lipophilic substance VM674, available from VisEn Medical, Bedford, Mass.) may be used in a fashion similar to indigo carmine and methylene blue were used relative to ureters, above, with reference to the absorptive properties of the fluorophore. The indocyanine green fluorophore may be conjugated with a lipophile to promote hepatobiliary excretion or injected directly into the gallbladder.

Figure 13:
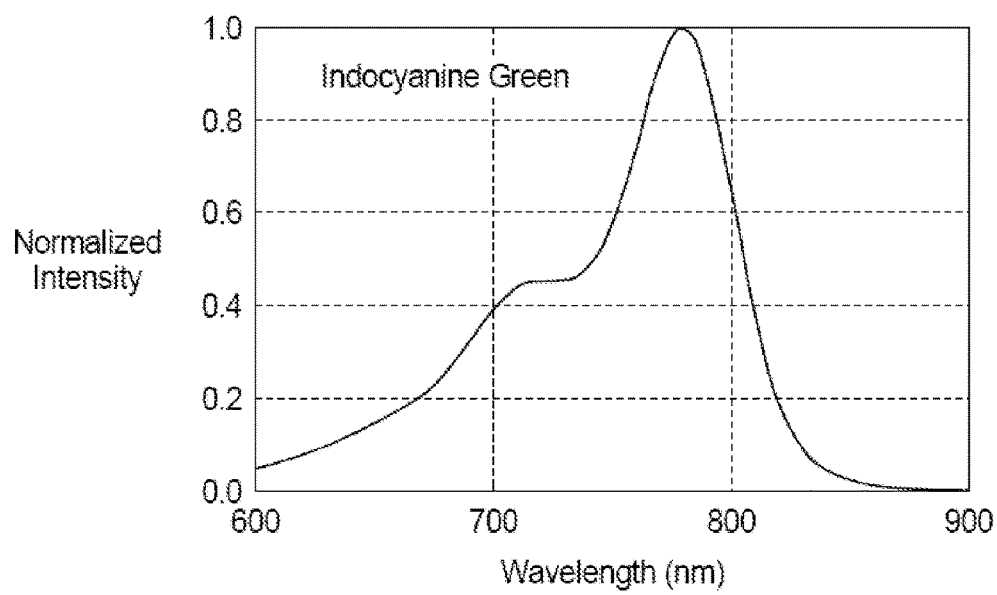
FIG. 13 is a chart illustrating the light absorption and emission spectra of indocyanine green.

FIG. 13 is a chart of the absorption and emission spectra of indocyanine green, with the absorption spectrum on the left and the emission spectrum on the right. It will be recognized that there is a significant narrow peak in the absorption spectrum at a wavelength of 780 nm, relative to the absorption at 660 nm, for example. It is believed that the detected light absorption at wavelengths of 780 nm and 660 nm will result in a ratio of between 5 and 10, while the ratio of light absorbed for blood or a blood vessel should be considerably less (e.g., potentially less than 1).

It may be possible to use other fluorophores or chromophores, depending on their absorption profiles. For example, methylene blue may be used. It will be recognized that methylene blue has been used previously for the coloration of the biliary tree. The methylene blue may be injected directly into the gallbladder, similar to the introduction method described above relative to indocyanine green.

Of course, where a particular fluorophore or chromophore has become established for use in procedures related to the gallbladder, this may provide an incentive to use the fluorophore or chromophore with the systems and methods described herein. That is, use of such a fluorophore or chromophore would simplify the procedure generally by eliminating the need to inject and detect multiple agents. Moreover, such a fluorophore may be used with intraoperative fluorescent imaging systems (such as the SPY Imaging System available from Novadaq of Mississauga, Ontario, Canada) so that the imaging system may provide a perspective of the entire cutting field, while the system according an embodiment of the present disclosure may provide information regarding the artifacts (in particular vessels) proximate to the working end of the surgical instrument.

Figure 14:
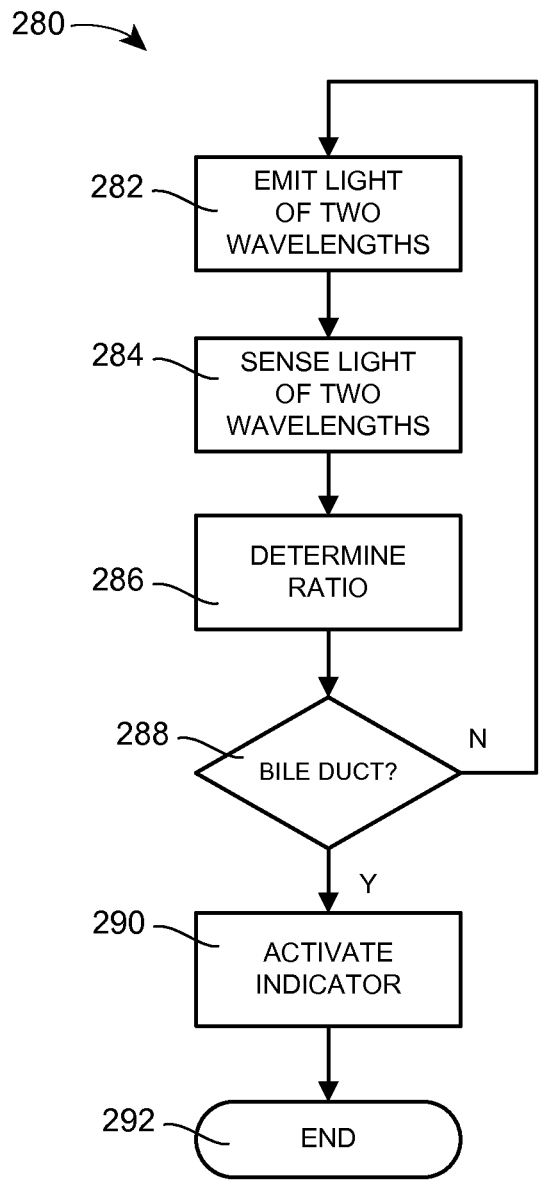
FIG. 14 is a flow chart of a method of detecting a bile duct according to an embodiment of the present disclosure, which method may be carried out using the system of FIG. 1.

As reflected in a flowchart of FIG. 14, a method 280 of determining if a bile duct is within a region 102 proximate to a working end 104 of a surgical instrument 106 is illustrated, and may be carried out using the surgical system 100 described in regard to FIG. 1. The method 280 begins at block 282, wherein light of at least two different wavelengths is emitted at the working end 104 of the surgical instrument 106, for example using the light emitter 110. The method 280 continues and/or also begins at block 284, wherein light of at least two different wavelengths is sensed at the working end 104 of the surgical instrument 106, for example using the light sensor 112. That is, the light may be emitted and detected successively using electronic multiplexing or simultaneously via use of optical filters (similar to the variation of method 150 illustrated in FIG. 3). The method 280 further includes determining a ratio of the light absorbed at the at least two different wavelengths at block 286, determining if an artifact is a bile duct at block 288 based on the ratio, and indicating if an artifact 120 within a region 102 proximate to the working end 104 of the surgical instrument 106 is a bile duct based on the ratio at block 290, which actions may be performed by the controller 114 and the indicator 130.

If it is determined at block 288 that the artifact is not a bile duct, the method 280 may return to block 282, to repeat the actions of blocks 282-288, as illustrated in FIG. 14. Furthermore, if the artifact is a bile duct and the indicator is activated at block 290, the method 280 may end at a block 292, as is also illustrated. For example, according to an embodiment of the method 280 where the indicator is a lockout device which disables the medical instrument 106, the method 280 may end at block 292 once the lockout device has been activated.

The method 280 may be varied in a fashion similar to the manner in which the method 150 of FIG. 1 was varied in the embodiments described in FIGS. 2-4. Furthermore, it may also be possible to use bile, in a fashion similar to the use of urea above (see FIG. 11), to determine whether an artifact is a bile duct. Bile has a local absorption maximum at 409 nm and a large absorption peak at 605 nm, and as such a ratio may be calculated that could be used to determine if an artifact is a bile duct.

However, the peak at 605 nm is much broader than the peak for indocyanine green, as illustrated in FIG. 13. As a consequence, the ratio between the absorption at the two wavelengths could result in a ratio that is not as easy to differentiate from the ratio for blood or a blood vessel, and could cause confusion between the hepatic artery and the bile duct, for example. Therefore, one embodiment would be to use a system that determines a ratio of the light absorbed at at least two different wavelengths and a characteristic pulsation. Even if the ratio did not provide a definitive determination that the artifact is a bile duct, the absence of a pulsatile signature in the artifact may permit its identification as a bile duct.

It will be noted that the presence of bile in the bile duct must be significant enough that the endogenous signal is adequately detectable. The human gallbladder empties at approximately 1 mL/min, with a maximum flow rate of 5 mL/min, while the average fasting flow rate in the cystic duct is 0.5 to 1.0 mL/min and the average flow rate after a meal is 2.0 to 3.0 mL/min. Such volumes should be sufficient to allow detection of the bile.

Figure 15:
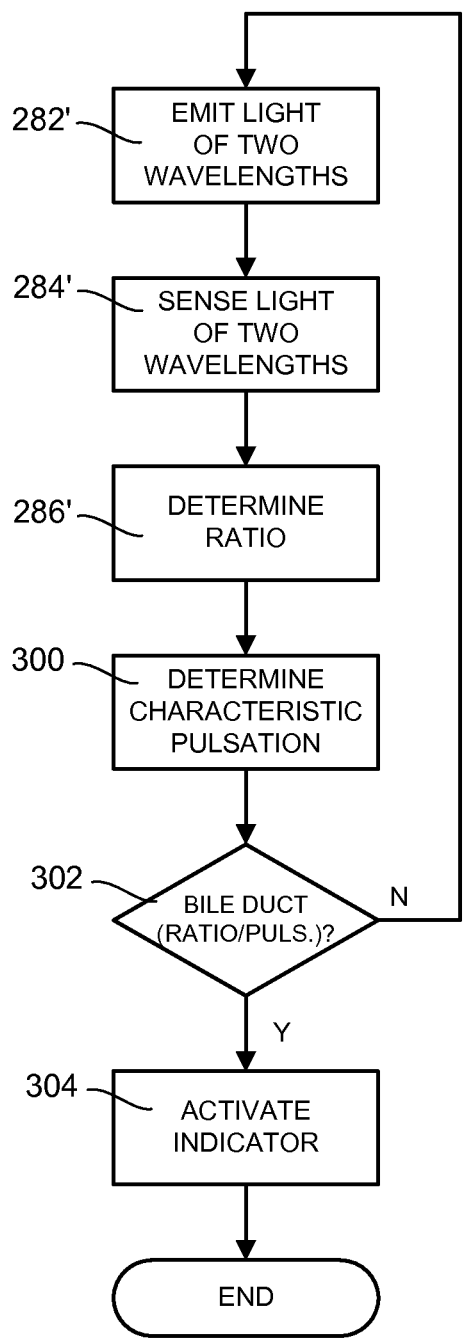
FIG. 15 is a flow chart of an alternative method of detecting a bile duct according to an embodiment of the present disclosure, which method may be carried out using the system of FIG. 1.

A method using bile in the detection of the bile duct is illustrated in FIG. 15, with the actions of blocks 282', 284', 286' being substantially similar to that of the embodiment of method 280 illustrated in FIG. 14. The method of FIG. 15 includes a block 300 wherein a characteristic pulsation of an artifact 120 within a region 102 proximate to the working end 104 of the surgical instrument 106 is determined based on the light detected by the light sensor 112. The method also includes a block 302 wherein a determination is made whether the artifact 120 is a bile duct based on the ratio and the characteristic pulsation, and a block 304 wherein an indication is made if the artifact 120 is a bile duct.

As another example, Patent Blue V may be used in regard to lymphatic vessel identification. Other alternatives include Evans blue and methylene blue, as well as indocyanine green. Patent Blue V and these other alternatives have the advantage, mentioned above, of being used in regard to lymphography at the present time, providing the incentives mentioned above for established fluorophores or chromophores.

Figure 16:
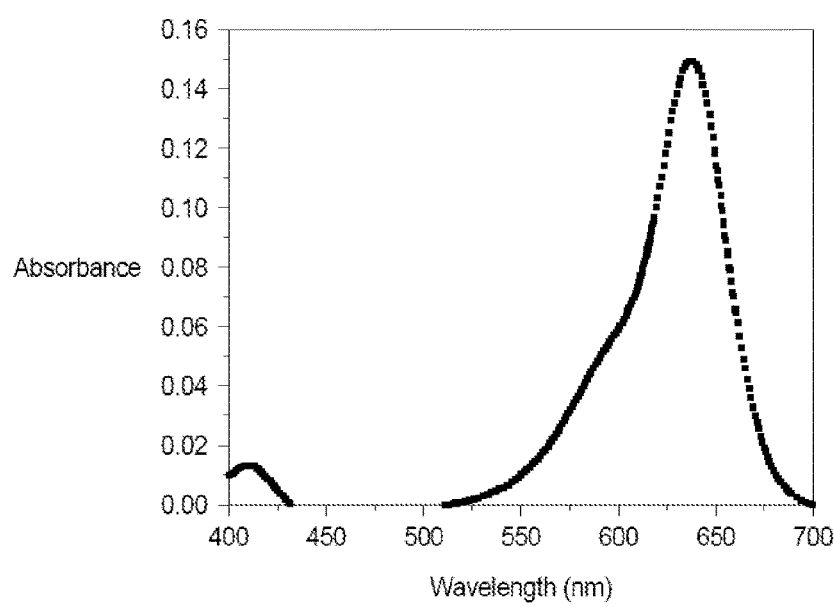
FIG. 16 is a chart illustrating the light absorption spectrum of Patent Blue V.

FIG. 16 is a chart of the absorption spectrum of Patent Blue V. It will be recognized that there is a significant peak in the absorption spectrum at a wavelength of 640 nm, relative to the absorption at 700 nm, for example. It is believed that the detected light absorption at wavelengths of 640 nm and 700 nm will result in a ratio of in excess of 10, while the ratio of light absorbed for blood or a blood vessel should be considerably less (e.g., potentially less than 1). As will be recognized from the discussion above, if indocyanine green is used instead, the ratio might be determined at 780 nm and 660 nm instead.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A surgical system used to determine if a ureter is within a region proximate to a working end of a surgical instrument, comprising:
   at least one light emitter disposed at the working end of the surgical instrument, the at least one light emitter adapted to emit light of at least two different wavelengths,
   at least one light sensor disposed at the working end of the surgical instrument opposite the at least one light emitter, the at least one light sensor adapted to detect light at the at least two different wavelengths, and
   a controller coupled to the at least one light sensor and adapted to determine a ratio of the light absorbed at the at least two different wavelengths,
   the controller being adapted to determine a characteristic pulsation of an artifact within a region proximate to the working end of the surgical instrument based on the light detected by the at least one light sensor, and to indicate if the artifact is a ureter based on the ratio and the characteristic pulsation.

2. The surgical system according to claim 1, wherein the at least one light sensor comprises a first light sensor adapted to detect light in the visible range and a second light sensor adapted to detect light in the near-infrared range.

3. The surgical system according to claim 2, wherein the first light sensor is adapted to detect light at 660 nm and the second light sensor is adapted to detect light at 810 nm.

4. The surgical system according to claim 1, wherein the at least one light sensor comprises a first light sensor adapted to detect light in the visible range and a second light sensor adapted to detect light in the infrared range above the near-infrared range.

5. The surgical system according to claim 4, wherein the second light sensor is adapted to detect light between 1400 nm and 1900 nm.

6. The surgical system according to claim 1, wherein the controller comprises a processor and memory, and the processor is programmed to determine a ratio of the light absorbed at the least two different wavelengths, to determine a characteristic pulsation of an artifact within a region proximate to the working end of the surgical instrument based on the light detected by the at least one light sensor, and to indicate if the artifact is a ureter based on the ratio and the characteristic pulsation.

7. The surgical system according to claim 1, further comprising a surgical instrument having a working end.

8. The surgical system according to claim 7, wherein the surgical instrument is a thermal ligature device.

9. A method of determining if a ureter is within a region proximate to a working end of a surgical instrument, comprising:
   emitting light of at least two different wavelengths at the working end of the surgical instrument;
   sensing light of at least two different wavelengths at the working end of the surgical instrument;
   determining a ratio of the light absorbed at the least two different wavelengths;
   determining a characteristic pulsation of an artifact within a region proximate to the working end of the surgical instrument based on the light detected by the at least one light sensor; and
   indicating if the artifact is a ureter based on the ratio and the characteristic pulsation.

10. The method according to claim 9, further comprising: administering a dye; and
    sensing light of at least two different wavelengths comprises sensing light at a first wavelength in the visible range and at a second wavelength in the near-infrared range.

11. The method according to claim 10, wherein administering a dye comprises continuously administering a dye intravenously throughout a surgery.

12. A surgical system used to determine if a vessel is within a region proximate to a working end of a surgical instrument, comprising:
    at least one light emitter disposed at the working end of the surgical instrument, the at least one light emitter adapted to emit light of at least two different wavelengths,
    at least one light sensor disposed at the working end of the surgical instrument opposite the at least one light emitter, the at least one light sensor adapted to detect light at the at least two different wavelengths, a controller coupled to the at least one light sensor and adapted to determine a ratio of the light absorbed at the at least two different wavelengths, the controller being adapted to determine a characteristic pulsation of an artifact within a region proximate to the working end of the surgical instrument based on the light detected by the at least one light sensor, and to indicate if the artifact is a vessel based on the ratio and the characteristic pulsation.

13. The surgical system according to claim 12, wherein the controller comprises a processor and memory, and the processor is programmed to determine a ratio of the light absorbed at the least two different wavelengths, to determine a characteristic pulsation of an artifact within a region proximate to the working end of the surgical instrument based on the light detected by the at least one light sensor, and to indicate if the artifact is a vessel based on the ratio and the characteristic pulsation.

14. The surgical system according to claim 12, wherein the at least one light sensor comprises a first light sensor adapted to detect light in the visible range and a second light sensor adapted to detect light in the near-infrared range.

15. The surgical system according to claim 14, wherein the first light sensor is adapted to detect light at 660 nm and the second light sensor is adapted to detect light at 810 nm.

16. The surgical system according to claim 12, wherein the at least one light sensor comprises a first light sensor adapted to detect light in the visible range and a second light sensor adapted to detect light in the infrared range above the near-infrared range.

17. The surgical system according to claim 16, wherein the second light sensor is adapted to detect light between 1400 nm and 1900 nm.

18. The surgical system according to claim 12, further comprising a surgical instrument having a working end.

19. The surgical system according to claim 18, wherein the surgical instrument is a thermal ligature device.

20. A method of determining if a vessel is within a region proximate to a working end of a surgical instrument, comprising:

emitting light of at least two different wavelengths at the working end of the surgical instrument;

sensing light of at least two different wavelengths at the working end of the surgical instrument;

determining a ratio of the light absorbed at the least two different wavelengths;

determining a characteristic pulsation of an artifact within a region proximate to the working end of the surgical instrument based on the light detected by the at least one light sensor; and indicating if the artifact is a vessel based on the ratio and the characteristic pulsation.

* * * * *